US00PP25573P3

(12) United States Plant Patent
Telch

(10) Patent No.: US PP25,573 P3
(45) Date of Patent: May 26, 2015

(54) RASPBERRY PLANT—VAJOLET PLUS CULTIVAR

(50) Latin Name: ***Rubus idaeus* L.**
Varietal Denomination: Vajolet Plus

(71) Applicant: Sant'Orsola Societa' Cooperativa Agricola (Italian Farmers Cooperative), Pergine Valsugana (IT)

(72) Inventor: Aldo Telch, Faver (IT)

(73) Assignee: Sant'Orsola Societa' Cooperativa Agricola, Pergine Valsugana (IT)

( * ) Notice: Subject to any disclaimer, the term of this patent is extended or adjusted under 35 U.S.C. 154(b) by 63 days.

(21) Appl. No.: 13/815,390

(22) Filed: Feb. 27, 2013

(65) Prior Publication Data

US 2014/0245503 P1 Aug. 28, 2014

(51) Int. Cl.
*A01H 5/00* (2006.01)

(52) U.S. Cl.
USPC ..... Plt./204

(58) Field of Classification Search
USPC ..... Plt./204
See application file for complete search history.

(56) References Cited

PUBLICATIONS

Kim S. Lewers, "Strawberry—USDA-ARS Genetic Improvement of Fruits and Vegetables Laboratory, Beltsville, MD", HortScience, vol. 47(5), May 2012, pp. 21.

*Primary Examiner* — Annette Para
(74) *Attorney, Agent, or Firm* — Ohlandt, Greeley, Ruggiero & Perle, L.L.P.

(57) ABSTRACT

The raspberry plant 'Vajolet Plus' was obtained by open pollination of Polka raspberry plants at Faver, (Cembra Valley, Province of Trento, Region Trentino—Italy). The new plant is a promocane variety producing two crops per year, wherein the fruits ripen on current season's cane in late to very late on previous season's cane early to medium. The resulting fruits are broad conical and vivid reddish orange in coloration.

3 Drawing Sheets

Genus and species: *Rubus idaeus* L.
Variety denomination: 'Vajolet Plus'.

BACKGROUND OF THE NEW VARIETY

A new and distinct cultivar of red raspberry (botanically known as *Rubus idaeus* L.) hereinafter referred to by the cultivar denomination 'Vajolet Plus' is disclosed. The new variety 'Vajolet Plus' was obtained by free pollination of individual Polka raspberry plants.

The new plant was created in 2003 at Faver, (Cembra Valley, Province of Trento, Region Trentino—Italy) and has been subject to selection in year 2005 and then asexually reproduced repeatedly by root cutting at Vigolo Vattaro (Province of Trento, Region Trentino—Italy), since year 2007. The characteristics of the new plant have been found stable and have been transmitted without change through succeeding (more than 6) asexual propagations (root cuttings).

SUMMARY OF THE INVENTION

The most outstanding and distinguishing characteristics of 'Vajolet Plus' are hereunder reported:

Primocane raspberry plant; growing the variety as floricane is to be preferred;
Good fruit colour and flavour;
Large and firm reddish orange berries;
Good shelf life.

The new plant can be propagated by: the use of suckers produced in a spawn-bed, root cutting and use of tissue culture techniques. The root cutting is to be preferred.

BRIEF DESCRIPTION OF THE PHOTOGRAPHS

The new red raspberry plant 'Vajolet Plus' is illustrated by the accompanying photographs showing typical specimens of the new variety in colour as true as reasonably possible to make the same colour illustrations of this character by conventional photographic procedures.

DETAILED DESCRIPTION

Figure 1:
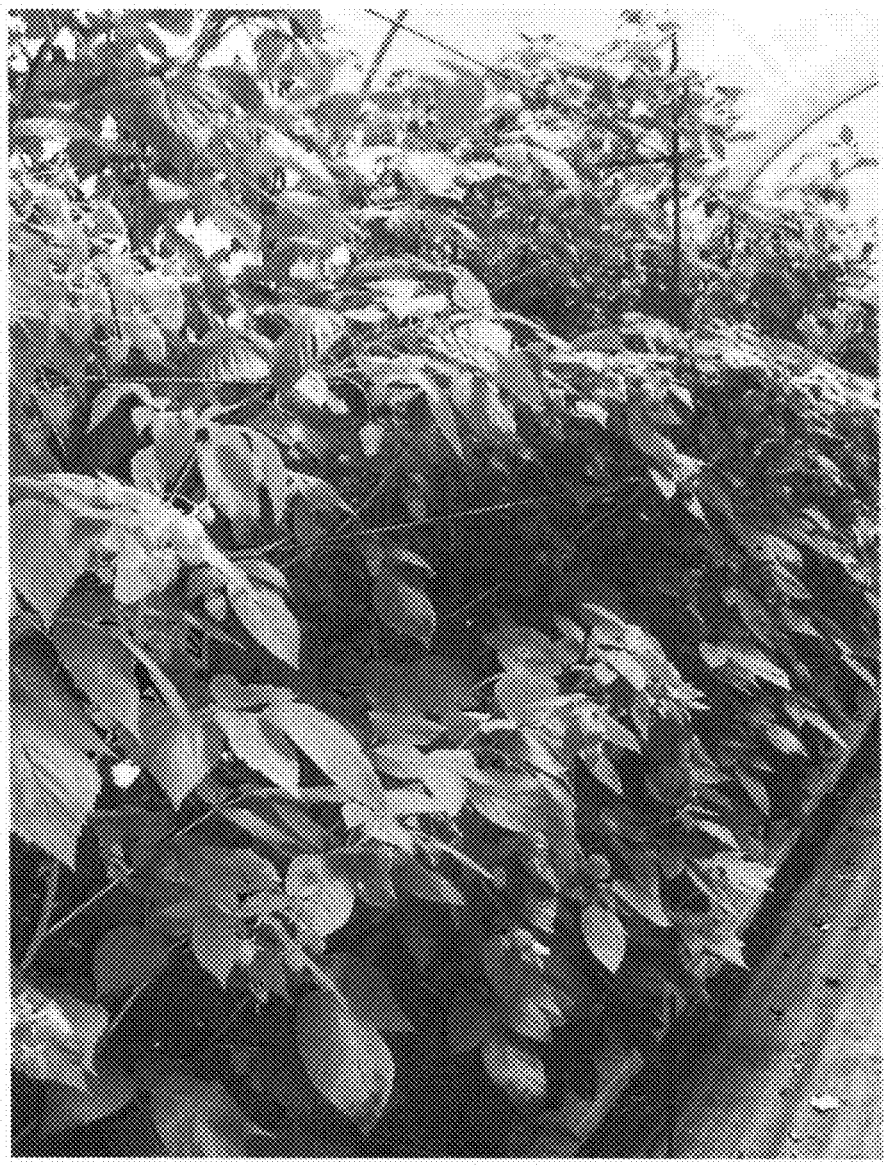
FIG. 1 is a view showing fruiting rows with the ripe and immature fruits borne on the tips.
Figure 2:
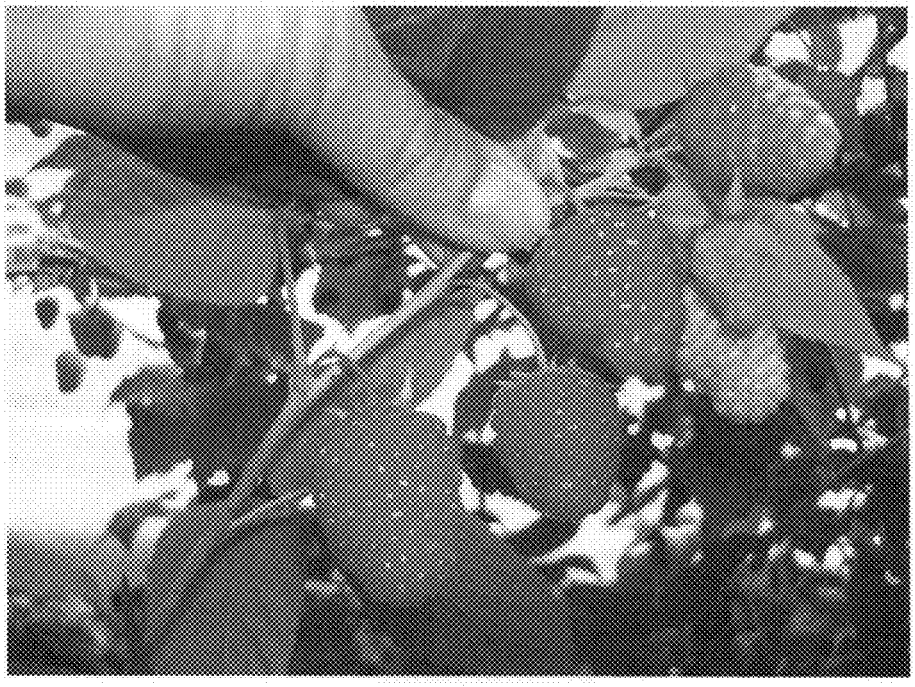
FIG. 2 is a view showing the fruit size, shape and colour at ripening.
Figure 3:
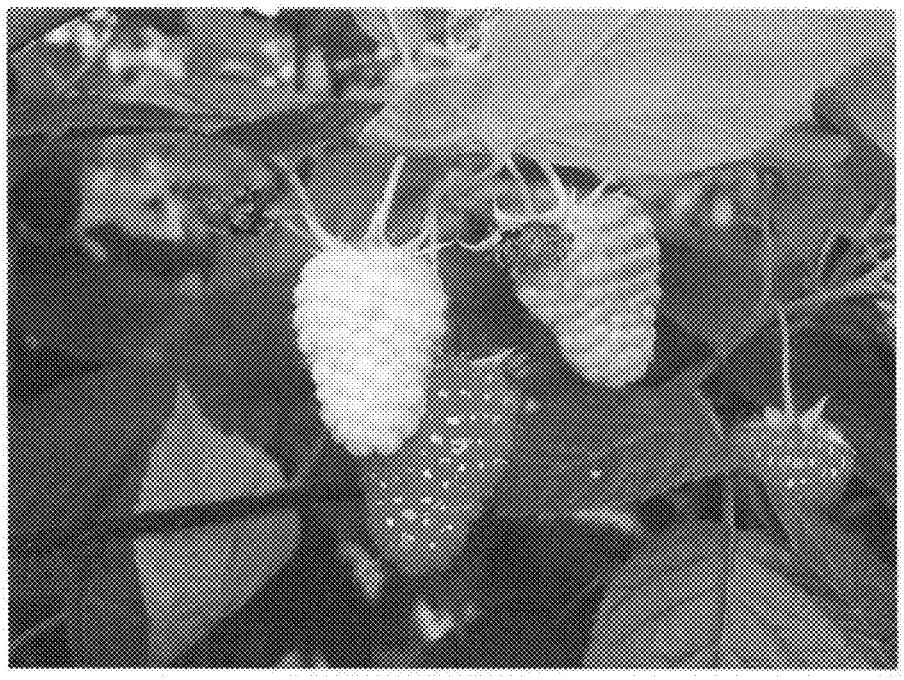
FIG. 3 is a view showing both the ripe and immature fruit size and shape.

The following detailed description set forth the distinctive characteristics of the new variety 'Vajolet Plus'. The performance of the new plant for retention of its distinctive characteristics has been evaluated through successive asexual propagations by root cutting in the Applicant's setting at Vigolo Vattaro, (Province of Trento, Region Trentino—Italy) under controlled conditions of temperature (minimal temperature 15° C. and maximal temperature 28° C.) in greenhouse, since 2007. The growing was the out of soil using peat as substrate. The canes have general upright habit and very strong vigour, with very good root system; adapted to lower-medium winter chill conditions such as in southern Italy. Furthermore, the plant has very high productivity in summer and lower productivity in autumn.

The plant assessment was performed for 3 years.

Colour references are primarily to The R.H.S. Colour Chart of The Royal Horticultural Society of London (Ed. 2007).

DETAILED BOTANICAL DESCRIPTION

A first assessment of the new plant was performed, in autumn, on a plant freshly planted in April of the same year. Then a second assessment was performed on the same plant at springtime of the following year (i.e. on a one year old plant). The plant observed has the following botanical description.

Classification

*Family*.—Rosaceae.

*Botanical*.—*Rubus idaeus* L.

*Common name*.—Raspberry.

Parentage: Open pollination of Polka raspberry plants. Polka is the female parentage.

Plant:

*Propagated*.—Root cuttings.

Primocane:

*Cane colour*.—Greyish Yellowish Green (RHS 194A).

*Spines*.—Present; the spines are dense, Moderate Reddish Brown (RHS 176B).

*Cane length*.—1.70 m (average).

*Cane diameter*.—13 mm (average).

*Cane texture*.—Hard to very hard.

*Internode length*.—Short to medium.

*Number of current season's shoots*.—Many to very many (30-40 on average).

*Very young shoot*.—Strong Reddish Purple (RHS 72A) of apex during rapid growth present.

*Dormant cane colour*.—Moderate Reddish Brown (RHS 166B).

Floricane:

*Cane colour*.—Moderate Brown (RHS 165A).

*Spines*.—Present; the spines are Greyish Red (RHS 176A).

*Cane length*.—1.70 m (average).

*Cane diameter*.—13 mm (average).

*Cane texture*.—Very hard.

*Internode length*.—Short to medium.

Leaves:

*Colour*.—Strong Yellowish Green (RHS 134B) on the upper surface and Light Yellowish Green (RHS 134D) on the lower surface.

*Shape*.—Concave; odd-pinnate and subdivided in 3-5 ovate and serrate small leaves with strong rugosity.

*Length*.—145 mm (average).

*Width*.—90 mm (average).

*Apex*.—Bluntish to pointed.

*Base*.—Orbicular ovate.

Flowers:

*Length*.—15 mm (average).

*Diameter*.—15 mm (average).

*Shape*.—Racemose.

*Primary colour*.—Greenish White (RHS 157D).

*Bloom*.—On the current season's cane, the blooming is weak and the flowers are large and white, and it begins later in the late to vey late season; on the previous season's cane, blooming is early and the flowers are large and white. In the Region of Trentino, the blooming on the current season's cane is in mid-July, while, on the previous season's cane, the blooming is in early May.

*Buds*.—Length: 8 mm (average); Width: 4 mm (average); Diameter: 4 mm (average); Shape: drop-shaped; Colour: Light Greyish Olive (RHS 195A).

*Petals*.—Length: 5 mm (average); Width: 3 mm (average); Shape: drop-shaped; Apex: rounded; Base: bluntish to pointed; Margin: smooth; Texture: thin; Colour: Greenish White (RHS 155C).

*Sepals*.—Length: 7 mm (average); Width: 5 mm (average); Shape: triangle shaped; Apex: pointed; Base: flat bottomed; Margin: smooth; Texture: medium thin; Colour: Pale Yellowish Green (RHS 193C).

*Peduncles*.—Length: 25 mm (average); Width: 2 mm (average); Diameter: 2 mm (average); Texture: medium thin; Colour: Greyish Yellowish Green (RHS 194B).

*Pedicels*.—Length: 20-50 mm; Width: 1-2 mm; Diameter: 1-2 mm; Texture: medium thin; Colour: Greyish Yellowish Green (RHS 194B).

Reproductive organs:

*Pistils per flower*.—Number: 60-80 (average); Ovary: oval shaped; Shape: flask shaped; Length: 10 mm (average); Width: 1 mm (average); Colour: Pale Yellowish Green (RHS 157C).

*Stamen*.—Number per flower: 70-90 (average); Length: 10 mm (average); Shape: thread; Colour: Greenish White (RHS 157D).

Fruit:

*Predominant shape*.—Broad conical.

*Weight*.—6-6.5 g (approximately).

*Size*(*ratio length/width*).—Large 25 mm/20 mm.

*Colour of ripe fruit*.—Vivid Reddish Orange (RHS 40B).

*Colour of fruit flesh*.—Vivid Reddish Orange (RHS 40B).

*Firmness*.—Medium to firm (0.13 kg/inch).

*Main bearing time*.—Both on previous year's cane in summer (mid June) and on current year's cane in autumn (mid September).

*Time of beginning the fruit ripening on previous season's cane*.—Early to medium; in the Region of Trentino, from about the last week in May until the first week of July.

*Time of beginning the fruit ripening on current season's cane*.—Late to very late; in the Region of Trentino, from about the last week of September until the end of October.

*Yield*.—1.4 kg/plant (average).

*Sugar*.—8.9° Brix.

*Storage capacity*.—'Vajolet Plus' has good shelf-life with good quality fruits that are suitable for both fresh and frozen retailing.

Pest and disease resistance: Strong canes resistant to pests and diseases; the plants needs few spray treatments for diseases and pest control.

Comparison with Commercial Cultivars

'Vajolet Plus' differs from the female variety 'Autumn Bliss' (U.S. Plant Pat. No. 6,597) in that 'Vajolet Plus' has broad conical shaped fruit, vivid reddish orange fruit, weighing between 6 g to 6.5 g, while 'Autumn Bliss' has an oval-conical shaped, medium to dark-red coloured fruit weighing between 3.5 g to 4.0 g.

'Vajolet Plus' is similar to the commercial variety 'Autumn Bliss'; however there are several differences as shown in Table 1.

TABLE 1

Comparison between 'Vajolet Plus' and 'Autumn Bliss'

| Characteristic | 'Vajolet Plus' | 'Autumn Bliss' |
|---|---|---|
| Plant vigor | strong | medium |
| Roots | very strong | medium |
| Fruit shape | broad conical | conical |

TABLE 1-continued

Comparison between 'Vajolet Plus' and 'Autumn Bliss'

| Characteristic | 'Vajolet Plus' | 'Autumn Bliss' |
|---|---|---|
| Productivity | high in summer | medium |
| Chill conditions | medium | lower |

What is claimed is:

1. A new and distinct variety of a primocane raspberry plant named 'Vajolet Plus', having berries that are large, firm, and vivid reddish orange, adapted to lower-medium winter chill conditions and having good tolerance to pests and diseases, as substantially herein shown and described.

* * * * *